(12) United States Patent
Al-Jaouni et al.

(10) Patent No.: US 9,861,675 B1
(45) Date of Patent: Jan. 9, 2018

(54) METHOD OF TREATING ISCHEMIC HEART DISEASE

(71) Applicant: KING ABDULAZIZ UNIVERSITY, Jeddah (SA)

(72) Inventors: Soad Khalil Al-Jaouni, Jeddah (SA); Seham Al Sayed Abdul-Hady, Jeddah (SA); Hany Mohamed Abd El-Malik El-Bassossy, Jeddah (SA); Numan Abdullah Salah, Jeddah (SA); Magda Mohamed Hagras, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 15/197,682

(22) Filed: Jun. 29, 2016

(51) Int. Cl.
*A61K 36/00* (2006.01)
*A61K 36/889* (2006.01)
*A61K 9/16* (2006.01)

(52) U.S. Cl.
CPC .............. *A61K 36/889* (2013.01); *A61K 9/16* (2013.01); *A61K 2236/15* (2013.01)

(58) Field of Classification Search
None
See application file for complete search history.

(56) References Cited

U.S. PATENT DOCUMENTS 9,623,067 B1 * 4/2017 Awad .................. A61K 36/889
2012/0148636 A1 * 6/2012 Berrido ................ A61K 8/0245
424/400

FOREIGN PATENT DOCUMENTS

WO   WO 2007/107787 A2   9/2007

* cited by examiner

Primary Examiner — Chris R Tate
Assistant Examiner — Russell Fiebig
(74) Attorney, Agent, or Firm — Richard C. Litman

(57) ABSTRACT

A method of treating ischemic heart disease can include administering a therapeutically effective amount of a composition including date seed nanoparticles to a subject in need thereof. Exemplary suitable dosage forms can include tablet, gel, paste, and suspension. The therapeutically effective amount of the composition including date seed nanoparticles can be about 2.0 mg/kg to about 2.5 mg/kg.

4 Claims, 3 Drawing Sheets

METHOD OF TREATING ISCHEMIC HEART DISEASE

BACKGROUND OF THE INVENTION

1. Field of the Invention

The present invention relates generally to methods for treating ischemic heart disease, and particularly to a method of treating ischemic heart disease using formulations including date seed nanoparticles.

2. Description of the Related Art

The fruit of the date palm (*Phoenix dactylifera* L.), also called "dates," are commonly consumed throughout the world, and particularly in the Middle East. Many studies indicate that palm date extracts have antioxidant and antimutagenic activities. The antioxidant activity could be due to the phenolic content in dates including p-coumaric, ferulic, and sinapic acids, flavonoids and procyanidins. Studies have further described use of a grinding machine to produce the powder of date seeds. However, grinding machines are not capable of producing nanoscale powder material.

Nanostructure materials with one or more dimensions in the 1-100 nm size range have distinct characteristics, which are unavailable in conventional macroscopic materials. For example, the reactions of nanomaterials such as nanoparticles with other materials can be more efficient owing to their high surface to volume ratios. Moreover, there are high percentages of atoms at the grain boundaries. Recent studies have found biomedical applications for nanoparticles in a variety of fields, including antibacterial agents, cell imaging, drug delivery and cancer therapy. Nanoformulations have demonstrated increased bioavailability, increased efficacy with lower doses of drug, decreased adverse effects, and decreased resistance.

Ischemic heart diseases are leading causes of mortality in developing as well as developed countries. The World Health Organization (WHO) has reported that cardiac disease will be the leading cause of disability and death by the year 2020. Myocardial ischemia occurs due to imbalance between oxygen supply to the myocardium and its demand leading to myocardial necrosis. One of the proposed mechanisms of the acute myocardial infarction pathophysiology is free radicals accumulation. Although treatment of angina is showing some progress, current therapies have only a limited impact on survival.

Thus, a method for the treatment of ischemic heart disease and/or complications thereof, thereby solving the aforementioned problems is desired.

SUMMARY OF THE INVENTION

A method of treating ischemic heart disease can include administering a therapeutically effective amount of a composition including date seed nanoparticles to a subject in need thereof. Exemplary suitable dosage foil is can include tablet, gel, paste, and suspension. For example, the therapeutically effective amount of the composition including date seed nanoparticles can be about 2.0 mg/kg to about 2.5 mg/kg for an adult subject weighing about 70 kg.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1A:
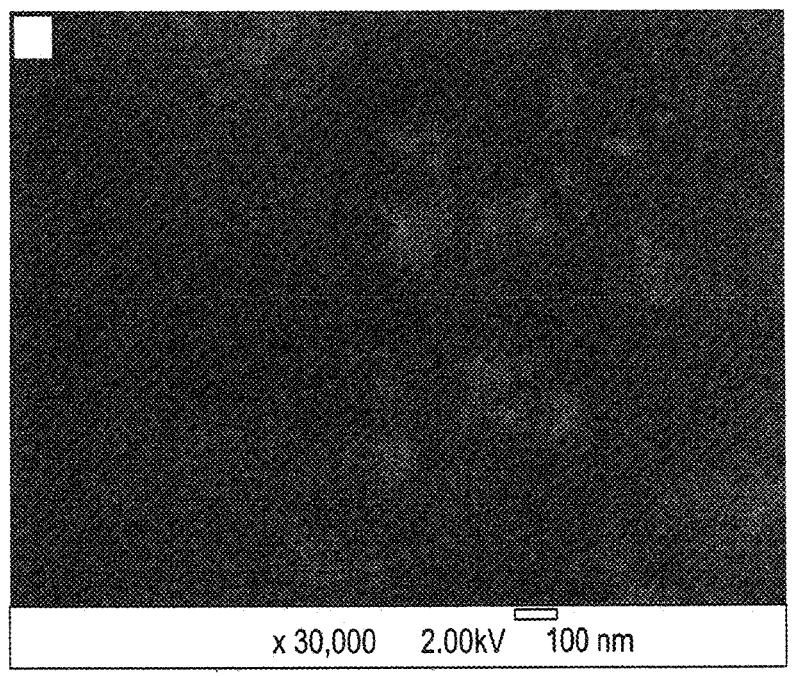
FIG. 1A-D shows the scanning electron microscopy (SEM) images at different magnifications for the date palm (Ajwa) nanoparticles by the method of the present invention.
Figure 1B:
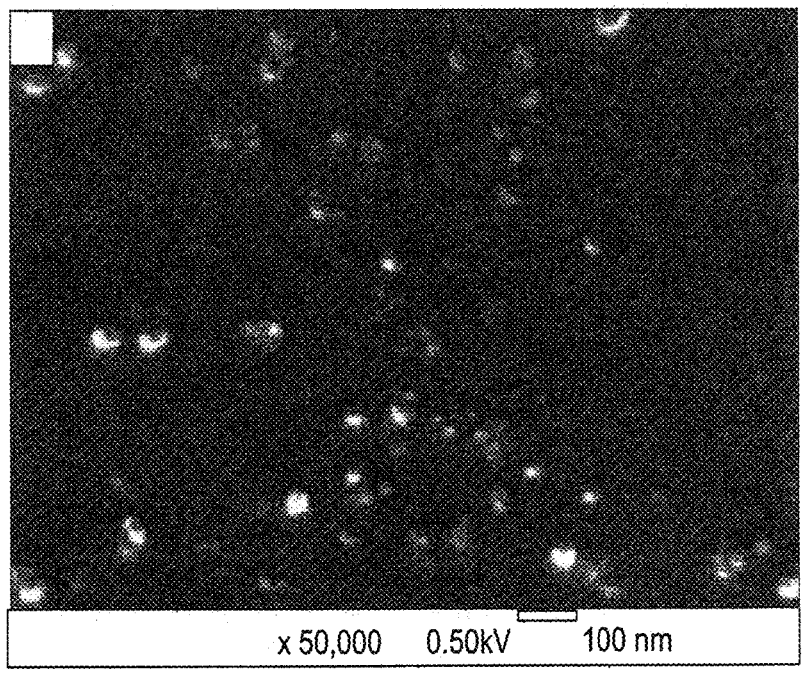
Figure 1C:
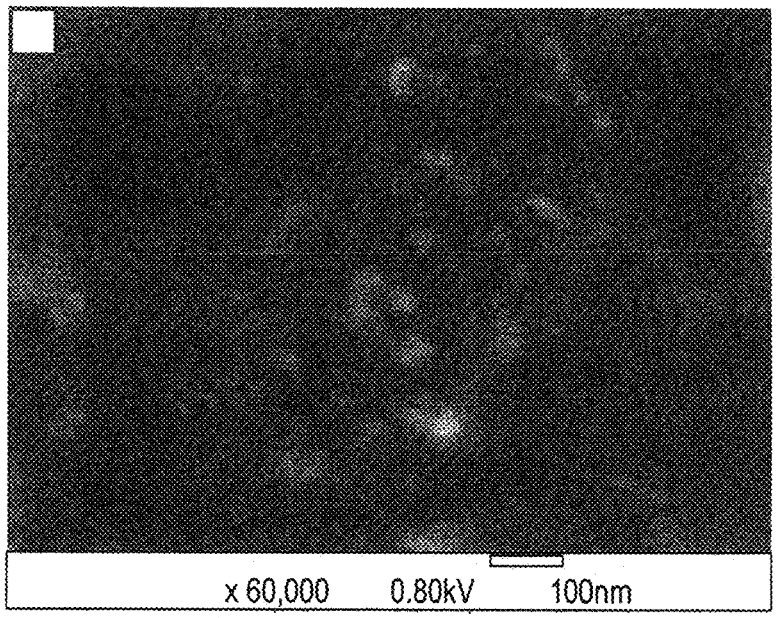
Figure 1D:
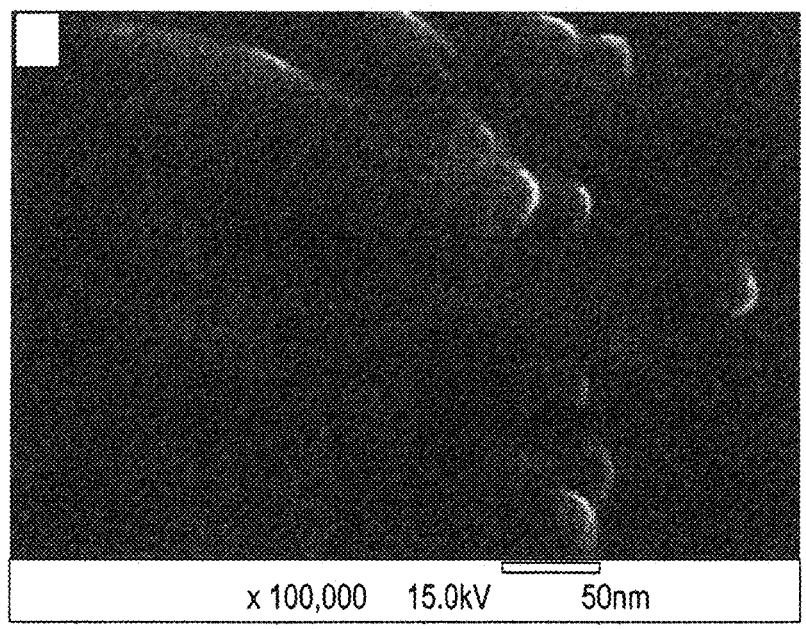

A method of treating ischemic heart disease can include administering a therapeutically effective amount of a composition including date seed nanoparticles to a subject in need thereof. Exemplary suitable dosage forms can include tablet, gel, paste, and suspension. The amount of the composition incorporated in a dose can be selected according to the examples provided herein and/or according to known principles of pharmacy. For example, the therapeutically effective amount of the composition including date seed nanoparticles can be about 2.0 mg/kg to about 2.5 mg/kg for an adult subject weighing about 70 kg.

A composition having date seed nanoparticles can include a mixture of date seed nanoparticles having an average particle diameter of less than 100 nm and the date palm fruit. As used, herein, date seed refers to the seed or pit of the date and the date palm fruit refers to the flesh of the date. Preferably, the date seed is the seed of the Ajwa date and date palm fruit is the flesh of the Ajwa date. Ajwa date palms are a species of *Phoenix dactylifera* L., and are commonly found in Saudi Arabia.

The mixture of the date palm seed nanoparticles and the date palm fruit can be active agents in a pharmaceutical composition for treating or preventing ischemic heart disease and/or complications associated therewith. For example, the composition can be useful for treating angina pectoris.

A pharmaceutical composition including the date palm seed nanoparticles and the date palm seed fruit can include one or more pharmaceutically acceptable carriers. Carriers are inert pharmaceutical excipients, including, but not limited to, binders, suspending agents, lubricants, flavorings, sweeteners, preservatives, dyes, and coatings. In preparing compositions in oral dosage form, any of the pharmaceutical carriers known in the art may be employed. For example, for liquid oral preparations, suitable carriers and additives include water, glycols, oils, alcohols, flavoring agents, preservatives, coloring agents and the like; for solid oral preparations, suitable carriers and additives include starches, sugars, diluents, granulating agents, lubricants, binders, disintegrating agents and the like. For parenteral use, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. Accordingly, the pharmaceutically acceptable carrier can include alcohol, dimethyl sulfoxide (DMSO), a physiological saline, a lipid based formulation, a liposomal formulation, a nanoparticle formulation, a micellar formulation, a water soluble formulation, a biodegradable polymer, an aqueous preparation, a hydrophobic preparation, a lipid based vehicle, or a polymer formulation.

A method of preparing the composition having nanoparticles of date palm seed can include separating date seeds from the fruit; drying the seeds; grinding the dry date seeds to form seed powder having a particle size ranging from 1 mm to 1000 mm; and ball milling the seed powder in a planetary ball mill at ambient temperature and pressure (high energy ball milling) to produce the date palm seed nanoparticles. The planetary ball mill can include a 250 ml steel cell, which oscillates at about 25 Hz. A ratio of the steel balls to the seed powder can be set to about 15:1 by weight. The steel balls can have a diameter of about 15 mm and weight of about 32 g. The date palm seed can include seeds from the fruit of the *Phoenix dactylifera* L. species known as "Ajwa" from Saudi Arabia. The ball milling method can produce date palm nanoparticle size ranging from about 1 nm to about 500 nm, preferably about 100 nm or less. The seed nanoparticles can be mixed with chopped Ajwa date fruit to provide a composition for treating and/or preventing angina pectoris. The proportion of the fruit weight to the seed nanoparticles can be equal to that of the original date's seed to fruit weight.

According to an embodiment the composition can be in tablet form. The method of preparing a tablet including the composition having nanoparticles of date palm seed can include mixing nanoparticles of the date palm seeds with a direct compressing material to form a mixture; passing the mixture through a sieve to obtain a powder of uniform size, adding a lubricating material to the powder; and compressing the powder using a tablet press machine to form a tablet. The tablet can have a hardness of 4.5 to 5.5 Kg. The direct compression material used can be avicel and the lubricating material can be magnesium stearate, for example.

According to an embodiment, the composition can be formulated as a suspension. The method of preparing a suspension of date palm seed nanoparticles can include separating date palm fruit from seeds; grinding the date palm fruit to provide semi-solid particles; mixing the semi-solid particles with the date palm seed nanoparticles (obtained as described above) to form a mixture; and milling the mixture in a planetary mill for about 20 minutes to form a paste of the date palm seed nanoparticle. A ratio of the semi-solid particles and the seed powder can be 1:1. A liquid vehicle can be added to the mixture to form the suspension. A preservative can be added to the suspension. Typically, the liquid vehicle is water or it can be an organic solvent such as alcohol.

According to an embodiment, the composition can be formulated as a gel. A suspension can first be prepared as described above. A cross-linked polyacrylate biopolymer powder can then be added to the suspension; followed by stirring. A triethanolamine can then be added followed by a preservative. The preservative can be methyl paraben, for example.

Mechanical ball milling is an effective technique for production of the nanocrystalline powders, without involving high temperature treatment. As used herein, the term "high energy ball milling" is a ball milling process where a powder mixture placed in the ball mill is subjected to high-energy collision from the balls. In this technique, starting powder particles are trapped between highly kinetic colliding balls and the inner surface of the vial, which causes repeated deformation, rewilding, and fragmentation of premixed powders resulting in the formation of fine, dispersed micro and nanoparticles in the grain-refined matrix. Planetary ball mills can be used to grind sample material down to very small sizes. A planetary ball mill includes at least one grinding jar which is arranged on a sun wheel. The direction of movement of the sun wheel is opposite to that of the grinding jars or cells.

The amount of the date palm nanoparticles incorporated in a dose can be selected according to the examples provided herein and/or according to known principles of pharmacy. An effective amount or therapeutically effective amount is specifically contemplated. By the term "effective amount", it is understood that, with respect to, for example, pharmaceuticals, a pharmaceutically effective amount is contemplated. A pharmaceutically effective amount is the amount or quantity of active ingredient which is enough for the required or desired therapeutic response, or in other words, the amount, which is sufficient to elicit an appreciable biological response when, administered to a patient. The appreciable biological response, i.e., treating and/or preventing ischemic heart disease, can occur as a result of administration of single or multiple doses of an active substance. A dose may comprise one or more dosage forms. It will be understood that the specific dose level for any patient will depend upon a variety of factors including the indication being treated, severity of the indication, patient health, age, gender, weight, diet, pharmacological response, the specific dosage form employed, and other such factors.

The following examples will further illustrate the processes of preparing the date palm nanoparticles and nanoformulations thereof.

Example 1

Preparation of the Nano-Pharmaceutical Formulation of *Phoenix dactylifera* L

Ajwa dates were collected from Al-Madina Al-Monawara city (Saudi Arabia) and stored in the refrigerator at 6° C. Date palm fruits were washed and dried. The seed (nucleus) of the Ajwa date was separated from the fruit, and dried at a temperature around 45° C. Then, these seeds were reduced to mm size using a fragmenting device (mixture, grinder etc.). After that these mm sized seeds were ball milled to the nanoscale size using the high energy ball milling technique. Nanoparticles of date seeds were ball milled for 20 hours. They were milled in steel cells (250 mL) using hardened steel balls (diameter 15 mm, weight 32 gm) in ambient atmosphere. The mechanical milling was performed in a horizontal oscillatory mill (Retsch, PM 400, Germany) operating at 25 Hz. The mixture ratio of steel balls and the grounded seeds powder was around 15:1 by weight. The milled material was used directly with no added milling media. Five balls were kept in each cell along with 10 gm of the sample powder.

Figure 2:
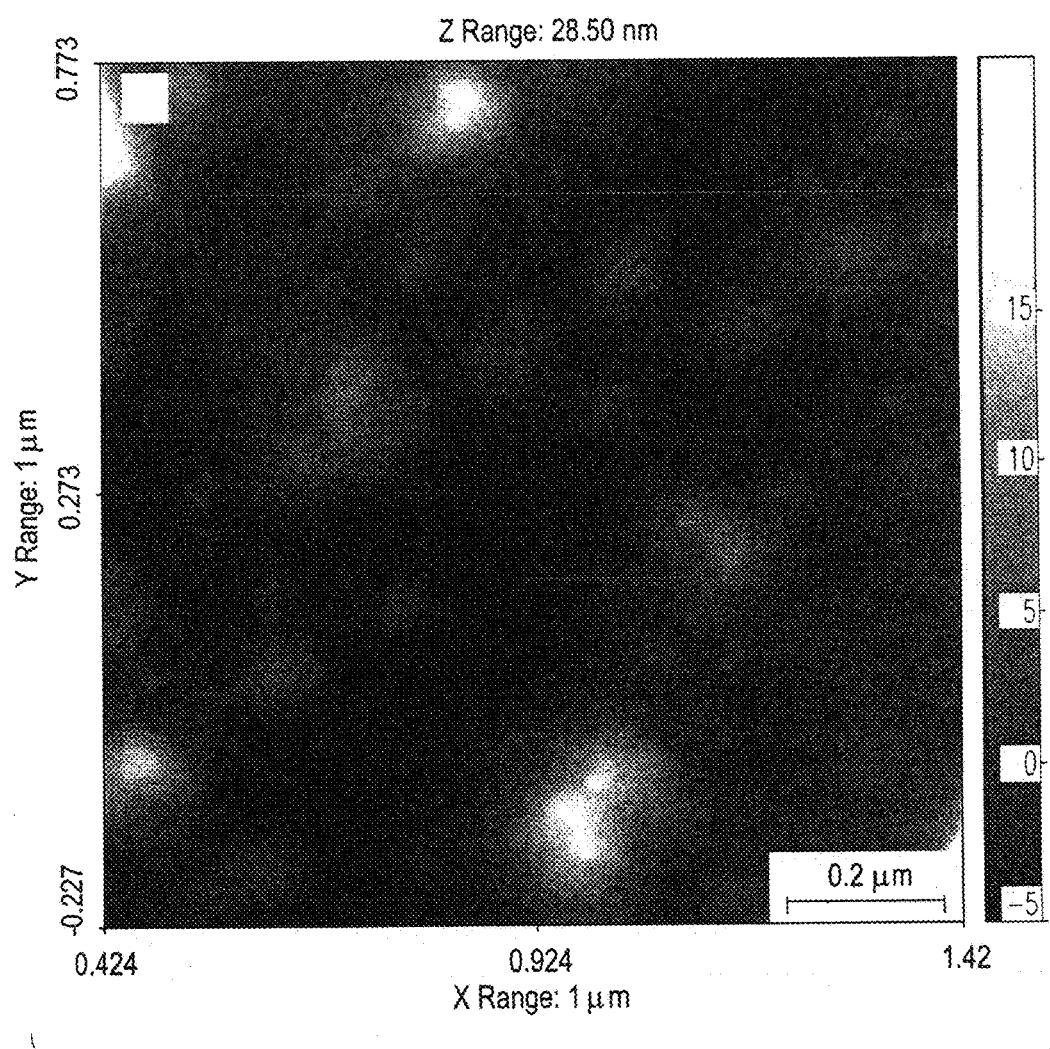
FIG. 2 shows the atomic force microscopy (AFM) image for the date palm seed nanoparticles.

The nanostructure form of the samples was characterized by a field emission scanning electron microscopy (SEM), JSM-7500 F (JEOL-Japan). FIGS. 1A-D show the scanning electron microscopy (SEM) images at different magnifications for the date palm (Ajwa) nanoparticles. The date palm nanoparticles were also analyzed by tapping mode atomic force microscopy (AFM) with scanning area of 1×1 µm. The instrument is a variable temperature UHVAFM/STM model XA 50/500, Omicron, Germany. FIG. 2 shows the atomic force microscopy (AFM) image for the date palm seed nanoparticles.

Example 2

Preparation of Nano-Dates Mixture

A mixture of nanoparticles of palm date "Ajwa" seed with fruit was prepared by chopping the fruit until it becomes soft and then it is mixed with the seed nanoparticles by keeping the proportion of fruit weight to nucleus nanoparticles equal to that of the original core weight to the fruit. Twenty dates were weighed separately to determine the mean weight of dates. Dates were separated into seeds and fruits, the seeds milled to nanoparticles as mentioned above in Example 1. The fruits were cut to very small pieces by a meat grinder to produce a semisolid form. The semisolid grinded fruit were mixed with the nanoparticles of seeds by the same ratio as the weight of the original dates in the planetary mixer for 20 minutes. As described in Example 6 below, a mixture of fruit paste and seeds nano-powder were administrated orally to rats with intra-gastric feeding tube at a dose of 13.3 mg/kg twice daily.

Example 3

Preparation of Tablet

The tablet was formed by mixing the nanoparticles of the date seed with direct compressing material such as avicel and passing it through sieve number 40, then mixing the powder with lubricating material such as magnesium stearates. This mixture was compressed using a single punch tablet press machine with oblong flat faced press. The compression force was adjusted to obtain tablets with hardness in the range of 4.5-5.5 Kg.

Example 4

Preparation of Suspension

The suspension was formed by mincing the fruit of the date using an extruder machine. The seed nanoparticles powder was mixed with the flesh in the planetary mixer, maintaining a ratio of its original form. The required amount of vehicle was added to the above mixture in the planetary mixer drop wise until a uniform suspension was achieved. Next 0.2% methyl paraben as preservative was added into the mixture. The suspension was transferred to a sterile glass bottle. The bottle was well shaken to ensure homogeneous suspension and labelled "shake before use."

Example 5

Preparation of Gels

The gel was formed by mincing the fruit of the date using an extruder machine. Nanoparticles were formed from the seed of the date palm as described above. The seed powder and the flesh were mixed in a planetary mixer, maintaining a ratio of its original form. The required amount of distilled water was added into the mixture in the planetary mixer dropwise until a uniform suspension was achieved. Carbopal 924 was introduced into the above suspension by slowly sprinkling a powder into vortex by rapid stirring, to prevent clumping. Once all of the powder was added, the stirring speed was reduced to decrease the possibility of entrapping air bubbles in the formulation. The Carbopol 924 was neutralized by adding triethanolamine to produce a suitable gel. Next methyl paraben (0.2%) was added as preservative.

Example 6

The Effect of Date Palm (Ajwa) Nanoformulations on Cardiac Function in Wistar Rats The effect of date palm (Ajwa) nanoformulations on cardiac function was studied on 10 male Wistar rats. An extra ten rats from the same type were used as a control untreated group. In the nano-formulation group, 13.3 mg/kg of the Ajwa nanoparticle mixture was given orally twice daily for 5 days. Vasopressin was injected (3 IU/kg; intravenous) to induce experimental cardiac ischemia and animals were investigated for hemodynamic, biochemical parameters and Immunofluorescence staining of Angiotensin II, Angiotensin I receptor, 4HNE (4-Hydroxynonenal) and collagen protein expression in both treated and untreated groups. The results showed that administration of the nano-pharmaceutical formulation of Ajwa for 5 days significantly decreased the systolic pressure, diastolic pressure, notch pressure, mean blood pressure and the heart rate compared to the control group. Pre-treatment with 13.3 mg/kg of Ajwa nano-formulation for 5 days lowered the elevated LVEDP compared to the control group. Systolic duration is more in the Ajwa treated group than the control group. Ajwa group showed a significant lowering of the uric acid level. Moreover, Ajwa group showed a significant decrease in the Angiotensin I receptors in both coronary and heart tissues compared to the control as detected by the immunofluorescent confocal microscope.

It is to be understood that the present invention is not limited to the embodiments described above, but encompasses any and all embodiments within the scope of the following claims.

We claim:

1. A method of treating ischemic heart disease in a subject in need thereof comprising administering to the subject a therapeutically effective amount of a composition containing *Phoenix dactylifera* L. (Ajwa date) seed nanoparticles.

2. The method of treating ischemic heart disease according to claim 1, wherein the composition further includes the *Phoenix dactylifera* L. fruit.

3. The method of treating ischemic heart disease according to claim 1, wherein the therapeutically effective amount provides a composition dosage of about 2 to 2.5 mg per kilogram/kg to the subject.

4. The method of treating ischemic heart disease according to claim 1, wherein the composition further includes a pharmaceutically acceptable carrier.

* * * * *